United States Patent [19]

Knoepfler

[11] Patent Number: 5,176,647

[45] Date of Patent: Jan. 5, 1993

[54] CATHETER DEVICE FOR PERFORMING A CHOLANGIOGRAM DURING A LAPAROSCOPY SURGERY

[76] Inventor: Dennis J. Knoepfler, 1383 Whittaker La., Amelia, Ohio 45102

[21] Appl. No.: 709,703

[22] Filed: Jun. 3, 1991

[51] Int. Cl.$^5$ .............................................. A61M 5/00
[52] U.S. Cl. .................................... 604/158; 604/159; 604/181
[58] Field of Search ............... 604/158, 159, 181, 183, 604/185, 104, 268, 272, 51, 52; 128/DIG. 12

[56] References Cited

U.S. PATENT DOCUMENTS

| | | | |
|---|---|---|---|
| 3,721,229 | 3/1973 | Panzer | 604/104 |
| 3,835,854 | 9/1974 | Jewett | 604/159 |
| 3,838,688 | 10/1974 | May et al. | 604/159 |
| 3,918,456 | 11/1975 | Patel | 604/104 |
| 3,995,628 | 12/1976 | Gula et al. | 604/159 |
| 4,342,313 | 8/1982 | Chittenden | 604/159 |
| 4,397,091 | 8/1983 | Gustavsson et al. | 604/159 |
| 4,559,041 | 12/1985 | Razi | 604/164 |
| 4,645,491 | 2/1987 | Evans | 604/158 |
| 5,059,183 | 10/1991 | Semrad | 604/280 |
| 5,071,412 | 12/1991 | Noda | 604/268 |

OTHER PUBLICATIONS

Arrow Kaplan ™ Balloon Clolangiography Catherization Set, Arrow International, Inc. 1991, Advertising brochure.
Arrow Kaplan ™ Balloon Clolangiogram Catherization Set. 1991 Promotional literature.
Advertising brochure for a Clolangiogram device manufactured by Laparomed, 1991.
Page from advertising brochure for Laproscopy cholecystectomy Instrumentation and equipment made by Solos Endoscopy. Jun. 1990.
Page from unidentified brochure for cholangiogram equipment.
Package cover for clip applier made by Auto Suture Co.
Advertisement for Laproscopy Equipment in Sep., 1991, issue of Contemporary Surgery.

Primary Examiner—Paul J. Hirsch
Attorney, Agent, or Firm—Wood, Herron & Evans

[57] ABSTRACT

A hand-held instrument for performing a cholangiogram during a laparoscopic surgical procedure is disclosed. The instrument includes a pistol-shaped housing having a cannula mounted at a forward end. Centrally located within the cannula and extending into the housing is a hollow catheter. Mounted within the housing are an advancing mechanism, a locking mechanism, and an injection system. The advancing mechanism incrementally extends the catheter from one end of the cannula and the locking mechanism holds the catheter at the extended position. The injection system expels contrast media from a reservoir within the handle of the housing into the catheter for injection into a cystic duct. Each of the systems within the housing can be independently operated by the hand holding the instrument. The end of the cannula distal from the housing includes a threaded bulge which is rotated by a wheel extending through the housing. Rotation of the wheel screws the threaded bulge into an incision on the cystic duct to facilitate the insertion of the cannula into the duct and to form a watertight seal which prevents leakage at the incision during injection of the contrast media.

15 Claims, 4 Drawing Sheets

CATHETER DEVICE FOR PERFORMING A CHOLANGIOGRAM DURING A LAPAROSCOPY SURGERY

FIELD OF THE INVENTION

This invention relates to instruments used in laparoscopic surgery.

BACKGROUND OF THE INVENTION

Laparoscopic surgery is being used more frequently because it is less intrusive to the patient's body which permits shorter hospital stays. One particular form of surgery which is especially adaptable to laparoscopic surgery is gall bladder removal.

In a typical laparoscopic surgical procedure for removing a gall bladder, short incisions are made through the abdominal wall of the patient for the insertion of the surgical instruments used to perform the surgery. The abdominal cavity is bloated by pumping a gas such as $CO_2$ into the abdominal cavity to provide the surgeons and their assistants with room to maneuver surgical instruments and a perspective from which a camera inserted into the cavity during the surgery can properly view the internal organs and abdominal wall. For each incision made through the abdominal wall, a trocar is inserted through the incision. The trocar provides a passageway for the surgical instruments through the patient's skin and abdominal wall and prevents the escape of the gas from the cavity during the surgery.

To provide the surgeon with a picture of what is occurring in the abdomen, an incision is made on the patient's umbilicus. After insertion of the trocar, a long laparoscope cylindrical lens of a camera is inserted through the trocar. The camera lens contains a light source to illuminate the organs and the picture generated by the camera is displayed on CRTs placed in the vicinity of the patient's upper body near the table. After viewing the display generated by the camera, the surgeon selects an appropriate spot on the upper right abdominal wall where a second incision is made and a trocar is inserted. This incision is used by a second surgeon or surgical assistant to aid the surgeon during the procedure. A third incision is made on the lower right side through which the second surgeon inserts instruments for assisting in exposing the gall bladder for dissection by the surgeon. The final incision is made in the upper midline (epigastrium) for the operative port through which the surgeon inserts various instruments used in performing the surgery.

To remove the gall bladder, the camera is used to locate adhesions on the abdominal wall which the surgeon removes with scrapping or cutting instruments inserted into the abdominal cavity. The liver is located and lifted to reveal the gall bladder underneath it. The cystic duct which leads into the gall bladder is clamped at a portion away from the gall bladder. The cystic artery is located and clamped to prevent excessive hemorrhaging in the abdominal cavity should a rupture of this artery occur. The gall bladder may be cut or burned loose by a laser. After the hemorrhage sites are cauterized to stop the bleeding, the gall bladder is located and pulled through the operative port in the abdominal wall. The trocars are removed and the incisions sutured. All clips, clamps, and instruments inserted in the abdominal cavity must be accounted by the surgical nurse.

While such a surgical procedure is effective for the removal of the gall bladder, ductal injuries or anatomical anomalies may not be readily discovered during such a surgical procedure. To provide the surgeon with this information during the surgery, a cholangiogram can be performed. A cholangiogram is an x-ray of the common bile duct which can alert the surgeon to previously undiscovered stones, anatomical anomalies which may require careful dissection, and ductal injuries which may lead to later complications following the gall bladder removal. If the cholangiogram is performed while the surgery is in process, the surgeon may remove the stones immediately and reduce the chance of post-operation common bile duct obstruction.

To perform a cholangiogram, a pair of micro-scissors are inserted into the abdominal cavity to dissect the cystic duct at a point between the gall bladder and where it is clamped. The micro-scissors are then removed. The surgeon inserts a gripping tool through a trocar while a nurse brings a tube leading from a syringe filled with contrast media into proximity with the cystic duct. At the forward end of the tube is mounted a cannula with a concentrically located catheter. The surgeon grips the end of the catheter extending from the cannula with the gripping tool and inserts it into the incision made by the micro-scissors. Using the inserted portion of the catheter as a guide wire, a portion of the cannula is inserted into the cystic duct. A clip is placed around the cannula and cystic duct to prevent leakage when the contrast media is injected.

At this point, all medical personnel except the surgeon and a technician leave the operating room. The technician places an x-ray film cassette under the patient's back and brings a mobile x-ray unit with a flexible C-arm over the patient's abdomen in the vicinity of the gall bladder. The surgeon then injects the contrast media through the tubing and catheter into the cystic duct which leads to the gall bladder. As the contrast media is injected, the technician takes a cholangiogram. After the technician has replaced the cassette with another one, the surgeon begins another injection so the technician can take a second cholangiogram. The technician removes the mobile x-ray machine and the other members of the operating team return.

The surgeon removes the clip from around the cannula and grips the cannula to remove it and then the catheter is withdrawn from the cystic duct. The nurse removes the tubing from the patient's abdomen through a trocar and the surgical procedure may proceed. The technician develops the cholangiograms and returns to the operating room to display them on light tables in the operating room. The surgeons may view them to ascertain if any additional surgical procedures are necessary.

While the information produced from a cholangiogram is important and useful to surgeons, very few surgeons conducting laparoscopic gall bladder removals regularly take them. This reluctance arises from the difficulties encountered in performing the procedure for taking cholangiograms. Most of the problems stem from the coordination required between the surgical team members to grasp and insert the catheter into the small incision in the cystic duct. This cooperation between team members is not only difficult because they must view the CRT to coordinate their instrument movements within the abdominal cavity, but they must manipulate articles that are very small. The diameter of the catheter is smaller than fish line and the incision in the cystic duct is correspondingly tiny. Such a procedure is roughly comparable to two people attempting to thread a needle by using barbecue tongs to hold the needle and thread. In some cases, inserting the catheter into the cystic duct through the small incision may take 30 minutes or longer. Such a time interval almost doubles the time necessary for the removal of a gall bladder.

What is needed is an expeditious method for performing a cholangiogram during a laparoscopic surgical procedure. What are also needed are instruments with which the surgical personnel can better coordinate their interactions to perform the cholangiogram.

SUMMARY OF THE INVENTION

The above problems associated with the taking of a cholangiogram during a laparoscopic surgical procedure are solved by an instrument built in accordance with the principles of the present invention. Such an instrument incorporates structural elements which perform multiple functions required for taking a cholangiogram in a single instrument to eliminate the need for coordinating activities between different members of the surgical team. The advantages of such an instrument include the elimination of using one instrument to perform a single function and then removing that instrument so it can be replaced by a second instrument to accomplish a second function. Another advantage of the present invention is to eliminate the number of people needed to perform a single activity such as inserting the catheter into the cystic duct.

It is an object of the present invention to provide one instrument for dissecting the cystic duct and inserting the catheter into the duct. In one embodiment of the present invention, a cannula having a lumen extending from one end to the other is provided with a hollow catheter that is centrally located within the lumen of the cannula and movable through the lumen of the cannula. One end of the cannula is angled with the edge at the juncture of the cannula and lumen sharpened. The cannula can be inserted through the trocar and the sharp edge of the cannula used to create the incision in the cystic duct. Without withdrawing the cannula, the catheter is then advanced into a cystic duct. Following insertion of the catheter, the cannula uses the catheter as a guide wire and is pushed into the cystic duct so a clip can be placed around the duct and cannula to seal the incision.

Another object of the present invention is to seal the incision in a cystic duct after the cannula has been inserted without requiring a clip. To meet this objective, the cannula has a threaded bulge near the angled end of the cannula. When the cannula is rotated the threaded bulge screws itself into the duct to effectively seal the incision from leakage. One advantage of this structure is the elimination of the second person to insert and place a clip about the cannula as well as the accounting for the clip within the abdomen.

It is an object of the present invention to provide a non-visual indicator of how far the catheter has been inserted into the cystic duct. One embodiment of the present invention includes an advancing mechanism which pushes the catheter through the cannula while providing acoustic and tactile feedback of the distance the catheter is advanced. One advantage of this device is that the surgeon may keep his eyes on the visual display without looking at the instrument to determine the catheter insertion distance.

Another object of the present invention is to selectively lock the catheter into a fixed relation to the cannula. The embodiment of the present invention includes a locking mechanism that secures the catheter after each increment of its advance so there is no slippage of the catheter between incremental advancements of the catheter.

Another object of the present invention is to substantially simultaneously release the locked relation between the catheter and the cannula while disengaging the catheter from the advancing mechanism. To accomplish this objective, a biasing member is provided that is operatively connected to the catheter and which urges the catheter against the advancing mechanism and the locking mechanism. When a release lever disengages the lock and advancing mechanism, the biasing member urges one end of the catheter away from the cannula which retracts the other end into the cannula. One advantage of this mechanism is easy removal of the cannula from the incision that can be performed by one person.

Another object of the present invention is to provide a mechanism for the person who makes the incision and inserts the catheter and cannula to inject contrast media into the cystic duct through the catheter. To achieve this objective of the invention, a connector is provided at the end of the catheter away from the cannula. This connector is then connected to a contrast media source so the contrast media may flow from the source through the connector and into the catheter.

Another object of the present invention is to provide a device for controllably pumping a fluid through the catheter. In accordance with the principles of the present invention, a hand operated plunger and reservoir are operatively connected to the catheter. The plunger is located so the surgeon controlling the cannula and catheter controls the flow of contrast media from the reservoir to the catheter without interfering with the other functions of the cannula and catheter.

Another object of the present invention is to provide a housing for the advancing mechanism, the locking mechanism, the release mechanism, and the pumping mechanism, that is connectable to the cannula and catheter so one person may conduct the cholangiogram procedure. To achieve this object, a pistol grip housing is provided in which the cannula is mounted at a forward portion of the housing with the catheter centrally located therein and extending through the housing to a connector located at the rear of the pistol grip. A trigger is connected to the advancing mechanism mounted in the housing so the surgeon can advance the catheter with the index finger alone. The advancing mechanism pushes the catheter forwardly through the cannula against the action of a spring mounted about the catheter within the housing which pushes against a collar concentrically mounted about the catheter. The locking mechanism engages the collar so the trigger activated advancing mechanism may return to its initial position for the next advancement of the catheter. The contrast media plunger is operated by the lower three digits of the hand on the pistol grip to pump contrast media from a reservoir within the pistol grip handle to a pressure actuated valve connected to the catheter near the connector to the outside fluid source. When the plunger acts on the reservoir, fluid flows from the reservoir through the valve and into the catheter for injection into the cystic duct.

The objects and features of the present invention will become more readily apparent from the following detailed description taken in conjunction with the accompanying drawings in which:

DETAILED DESCRIPTION OF THE PREFERRED EMBODIMENT

Figure 1:
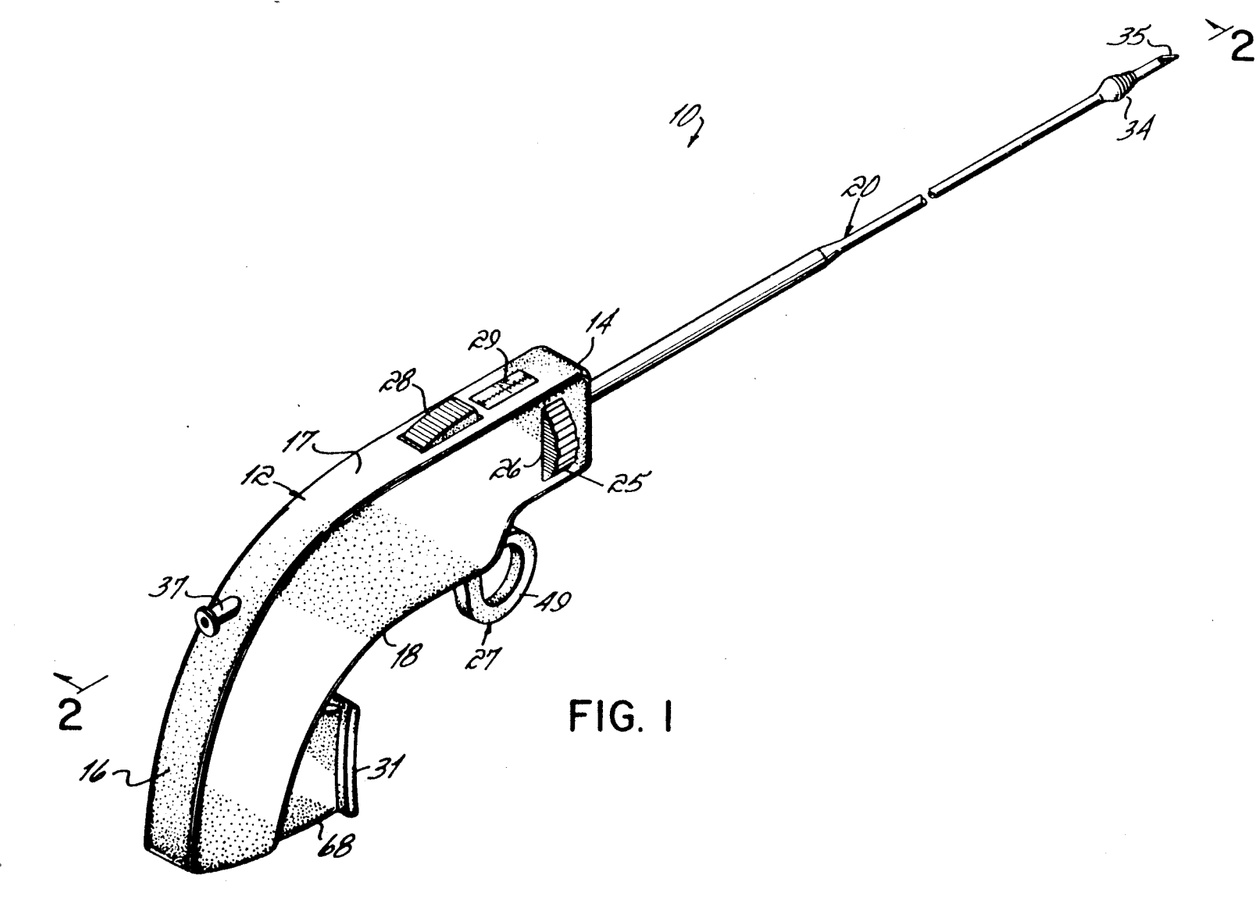
FIG. 1 is a perspective view of the preferred embodiment of the present invention.
Figures 2, 2A:
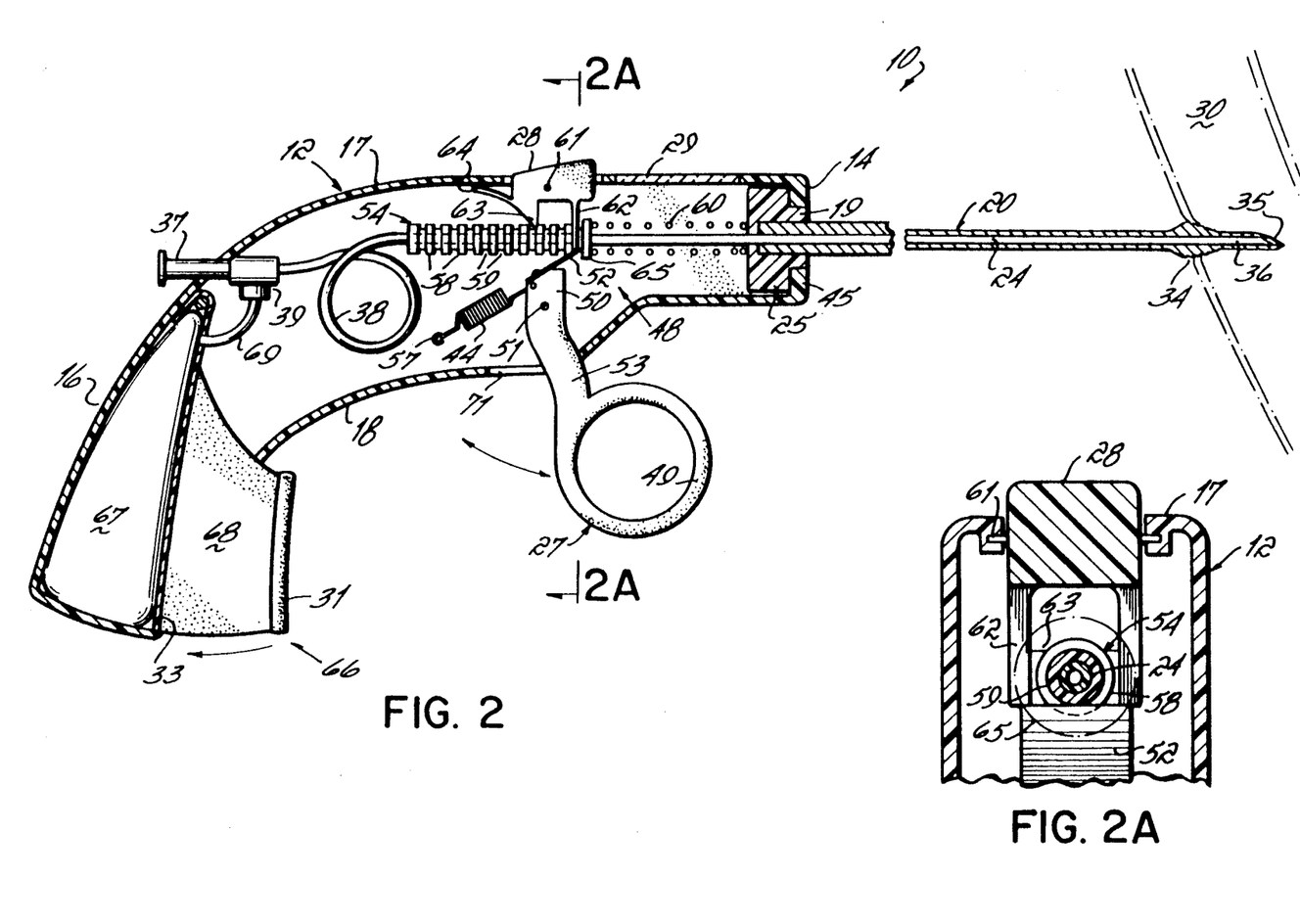
FIG. 2 is a fragmentary, cross-sectional view of the preferred embodiment of the invention taken along lines 2—2 of FIG. 1.
FIG. 2A is a partial cross-sectional view taken along lines 2A—2A in FIG. 2.

A preferred embodiment of a cholangiogram instrument used for injecting contrast media into a gall bladder through the cystic duct is shown in FIGS. 1 and 2. The instrument 10 includes a pistol shaped housing 12 having forward portion 14, rearward handle portion 16, top surface 17 and lower surface 18. Mounted to a dial hub 19 in forward portion 14 is a cannula 20 which contains a catheter 24. Dial wheel 25 of hub 19 extends through opening 26 to provide the surgeon with control of cannula 20 as explained below.

A trigger 27 which controls an advancing mechanism extends below lower surface 18 while lock and release arm 28 is exposed through top surface 17. Also mounted in top surface 17 is a transparent depth gauge 29 through which the surgeon can determine the length of catheter 24 inserted into duct 30, as explained below. Plunger actuator 31 extends forwardly of handle 16 for injecting contrast media from a reservoir in housing 12 through catheter 24 as described in detail below.

Housing 12 is preferably constructed of a resilient, lightweight plastic material so the hand of the surgeon operating the instrument does not fatigue easily. The surface of housing 12 has a finish which provides a good gripping surface for the surgeon through the sterilized, plastic gloves usually worn during surgery. Cannula 20 is mounted at one end to forward portion 14 of housing 12, extends forwardly to a threaded bulge 34, and terminates at an angled end 35. A lumen or bore 36 extends through cannula 20 and the edge where lumen 36 and cannula 20 meet at angled end 35 is sharpened. Cannula 20 is preferably constructed from surgical stainless steel so the sharpened edge at end 35 retains its cutting edge.

Mounted near the forward portion of housing 12 is the trigger 27 which is used to drive the advancing mechanism for the catheter 24 which is described in more detail below. Lock and release arm 28, depth gauge 29, and a leur lock 37 are mounted in or through top surface 17 of housing 12. Located along lower surface 18 near the rearmost portion of pistol grip housing 12 is plunger actuator 31. Plunger actuator 31 is connected by a plunger arm 68 to a plunger 33 mounted within handle portion 16 of housing 12. Lock and release arm 28, leur lock 37, plunger 33, and trigger 27 are all constructed from resilient plastic materials to decrease the weight of the instrument and reduce the cost of its construction.

The internal structure of the preferred embodiment of the present invention which accomplishes the multifunctional and compact design of the present invention is depicted in FIG. 2. Centrally located within cannula 20 is the hollow catheter 24 which extends through housing 12 and forms a loop 38 before connecting with valve 39. Cannula 20 fits sufficiently snug about catheter 24 that no appreciable amount of gas escapes from the abdominal cavity through cannula 20. Cannula 20 is fixedly mounted into dial hub 19 of dial wheel 25. Dial wheel 25 is rotatably secured against front wall 45 by a spring 60.

Catheter 24 is preferably a 4F or 5F size catheter with a preferable length of 25-30 centimeters, but any length sufficient to extend from valve 39 through housing 12 and cannula 20 into the cystic duct 30 by approximately 1.5-2 centimeters is satisfactory. Loop 38 in catheter 24 at its rearward end is preferably provided for storing the extra length of catheter needed for extension into the cystic duct 30. The catheter 24 is preferably inflexible to prevent kinks or pinching of the catheter which may block the flow of fluid through the catheter 24. While the preferred cannula is approximately 5 mm for an eight centimeter section extending from housing 12, then narrows to a diameter of approximately 3.5 to 4 mm to threaded bulge 34 and then resumes the reduced diameter on the other side of bulge 34, other dimensions could be used so long as they maintain a fluid tight seal in the trocar and do not block the surgeon's view of the duct. The construction of such catheters are well known within the art.

Advancing mechanism 48 for extending the catheter beyond sharp end 35 of cannula 20 includes trigger 27 having a trigger ring 49 and trigger arm 53 which is pivotally mounted about pin 51. The distal end 50 of trigger arm 53 is preferably notched, although other connecting methods could be used, to connect one end of driving link 52 to arm 53 while the other end of link 52 abuts a collar 54. Spring 44 is mounted to housing 12 by a pin 57 at one end and the other end of spring 44 connects to trigger arm 53 through a hole in distal end 50.

Collar 54 is concentrically and fixedly mounted about catheter 24. Collar 54 is cylindrical with regularly spaced apart, circular ridges 58 that are concentrically formed about collar 54. Ridges 58 are preferably spaced approximately 0.2 centimeter apart. Interposed between the forward end of collar 54 and front wall 45 of housing 12 is spring 60 which is concentrically mounted about catheter 24. The forwardmost ridge which abuts spring 60 has a larger diameter than the other ridges mounted about collar 54. When trigger 27 is squeezed rearwardly so it clockwise pivots about pin 51 the forward end of link 52 is urged against collar 54 to advance the catheter against the rearward bias of spring 60.

In the preferred embodiment of the invention, transparent depth gauge 29 permits the surgeon to view the top edge of the forward end of collar 54. Gauge 29 is inscribed with lines spaced approximately 0.2 centimeters apart. As collar 54 is advanced, the juxtaposition of collar 54 and the lines on gauge 29 provide a visual indication of how far catheter 24 has been advanced from cannula end 35. Alternatively, a known catheter having lineations at its discharge end may be used so the surgeon can observe the lineations as they enter the incision to determine the amount of catheter extension.

Figures 3, 5:
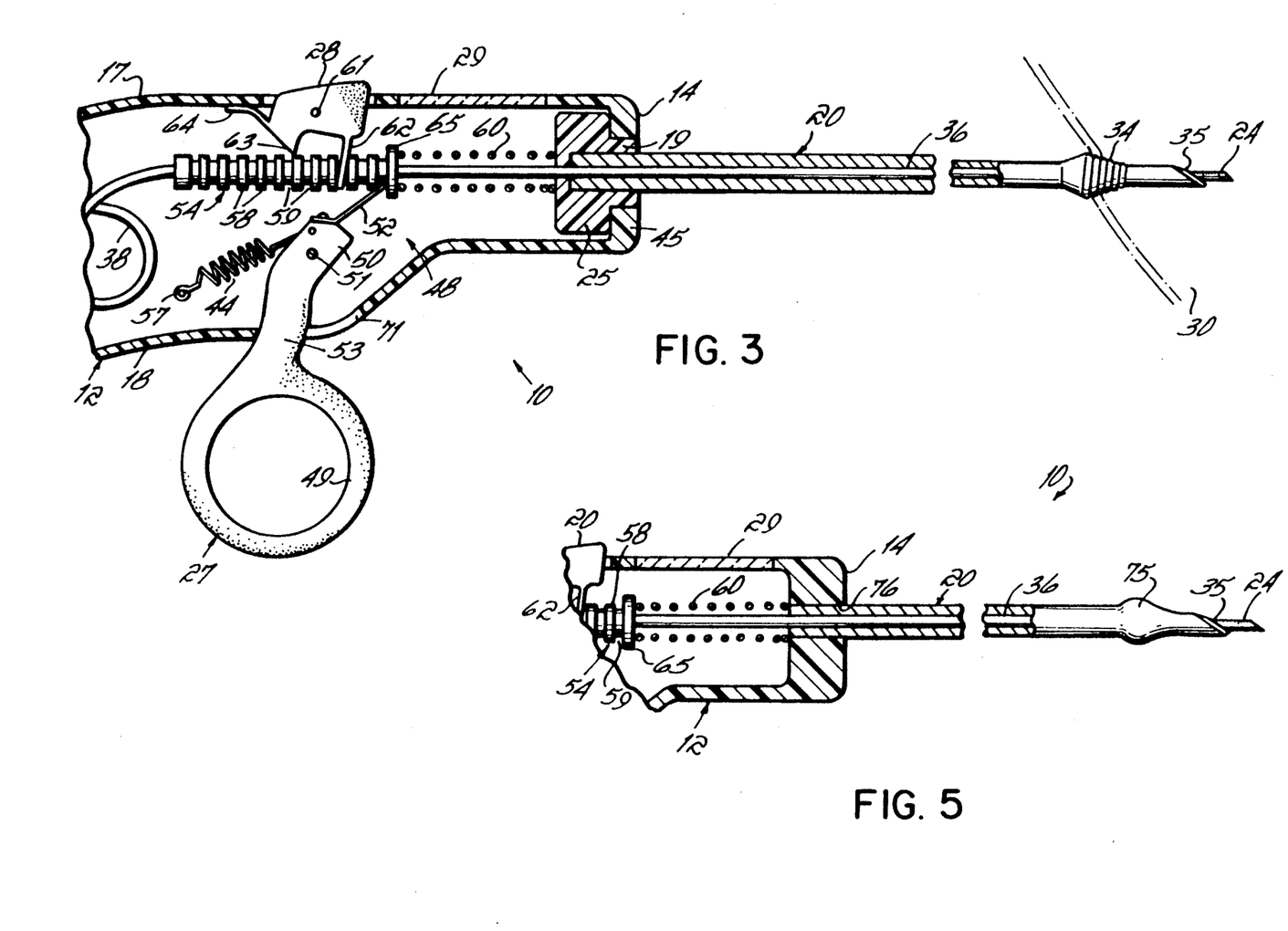
FIG. 3 is a partial cross-sectional view of the forward portion of the preferred embodiment of the invention which illustrates the operation of the advancing mechanism.
FIG. 5 is a partial cross-sectional view of an alternative embodiment which shows a cannula which may be used in an apparatus constructed in accordance with the principles of the invention.

The internal structure shown in FIGS. 2 and 3 also includes lock and release arm 28 which is pivotally mounted about a pin 61. Arm 28 has a forward release member 62 and a rearward locking member 63. End 64 of locking member 63 generates a downward bias against collar 54 which urges the locking arm 63 into engagement with collar 54. Release member 62 of lock and release arm 28 is laterally offset so it passes outside the diameter of the ridge 58 except the forwardmost ridge 65 of the collar. The lower end of the member 62 extends towards collar 54 from member 62 to abut the forward end of link 52 along its top edge.

The structural relationships of the ridges on collar 54 with release member 62 and link 52 are best shown in FIG. 2A. Link 52 extends across a portion of the lowermost circumference of one of the ridges 58. Release member 62 extends downwardly along each side of the collar to abut link 52. The release member is outside of the circumference of collar 58 so it does not interfere with the rearward movement of collar 54 when the catheter is retracted. Release member 62 is within the circumference of the forwardmost ridge 65 (shown in phantom) to stop the rearward movement of collar 54 during withdrawal of the catheter.

FIG. 2 shows an injection system 66 mounted in the rearward portion of housing 12 which includes a plunger actuator 31, reservoir 67 and valve 39. Interposed between reservoir 67 and lower surface 18 of housing 12 is a plunger 33 that is connected to plunger arm 68. Plunger 33 is hingedly mounted within housing 12 so the plunger lies adjacent reservoir 67 along the entire length of one side. Actuator 31 is connected to the plunger arm 68 to rotate the plunger against collapsible reservoir 67 to force fluid from the reservoir, up through conduit 69 to valve 39. Valve 39 prevents the fluid from flowing towards the leur lock and directs the expelled fluid into the catheter. Reservoir 67 is sufficiently sized to contain approximately 40 cc of contrast media since the typical two cholangiogram procedure requires two injections of approximately 15 cc of media. The excess capacity provides a reserve capacity.

To prepare the gall bladder for a cholangiogram, the surgeon inserts cannula 20 through one of the trocars and cuts an incision into the cystic duct 30 with the sharp surface of lumen 36 at end 35. Once the incision is made, catheter 24 is advanced through the incision into the cystic duct 30 by squeezing trigger 27.

As trigger 27 is squeezed, trigger arm 53 rotates clockwise about pivot 51 against the bias of spring 44 to urge driving link 52 against collar 54 (FIG. 3). This urging moves collar 54 forward and advances catheter 24 beyond cannula end 35 into the cystic duct 30. In the preferred embodiment of the invention, opening 71 permits lever arm 53 to move a distance which advances collar 54 and catheter 24 by one ridge or approximately 0.2 centimeter. To prevent catheter 24 from slipping back into housing 12, locking member 63 engages collar 54 to hold it against the rearward bias of spring 60 while trigger 27 is pulled in the counterclockwise direction by spring 44 for the next incremental advance.

The holding action of locking arm 63 is best shown in FIG. 3. As one of the ridges 58 pushes locking arm 63 upwardly it also slides underneath the locking arm as collar 54 moves forward. When ridge 58 of collar 54 passes forwardly of locking arm 63, the locking arm falls into a gap 59 between adjacent ridges 58. In the preferred embodiment of the invention, opening 71 through which lever arm 53 extends is sized so that when lever arm 53 contacts housing 12 at the rearmost portion of opening 71, one of the ridges 58 have passed forwardly of locking arm 63. Releasing trigger 27 permits spring 44 to retract from the extended position it reached when arm 53 was pivoted clockwise to rotate trigger 27 in a counterclockwise fashion about pivot 51. As arm 53 so rotates, link 52 disengages from collar 54 and the biasing action of spring 60 urges collar 54 rearward. This causes the ridge just forward of locking arm 63 to clockwise rotate lock and release arm 28 about pivot pin 48 to compress locking arm 63 against housing 12 until locking arm 63 stops the rotation. Thus, trigger 27 returns to its forward position while collar 54 and catheter 24 remain at the position to which they were extended without slipping.

If leur lock 37 is connected to an outside fluid source (not shown) such as saline solution container, the saline solution flows through leur lock 37, valve 39, and catheter 24 to discharge the saline solution from the forward end of the catheter. This flow is used to check the flow path through the catheter into the cystic duct 30. By clockwise rotating dial wheel 25 in the preferred embodiment, the threads about threaded bulge 39 are advanced, if the threads are a right-hand thread, so the bulge screws itself into the incision. By pushing housing 12 forward, the surgeon causes cannula 20 to follow the inserted catheter like a guide wire so threaded bulge 34 of cannula 20 is inserted into the duct.

Bulge 34 of cannula 20 is sufficiently sized to distend the cystic duct when inserted therein and the irregular surface of the threads are gripped by the duct to form a fluid-tight seal between the duct and the threaded bulge. In the preferred embodiment of the present invention, the threaded bulge has an outside diameter of 3.5 to 4 mm at its maximum width and is inscribed with a right-hand thread, though other dimensions and thread twist directions could be used. The bulge 34 is also preferably located within 4 to 12 millimeters of cannula end 35.

An alternative embodiment of cannula 20 is shown in FIG. 5 and is fixedly mounted within bore 76 in housing 12. The bulge 75 of this embodiment is smooth rather than threaded. The smooth surface of bulge 75 may permit fluid to flow over the bulge and leak from the duct at the incision. To prevent this, a clip may be applied to press the duct against the bulge to seal the incision.

Figure 4:
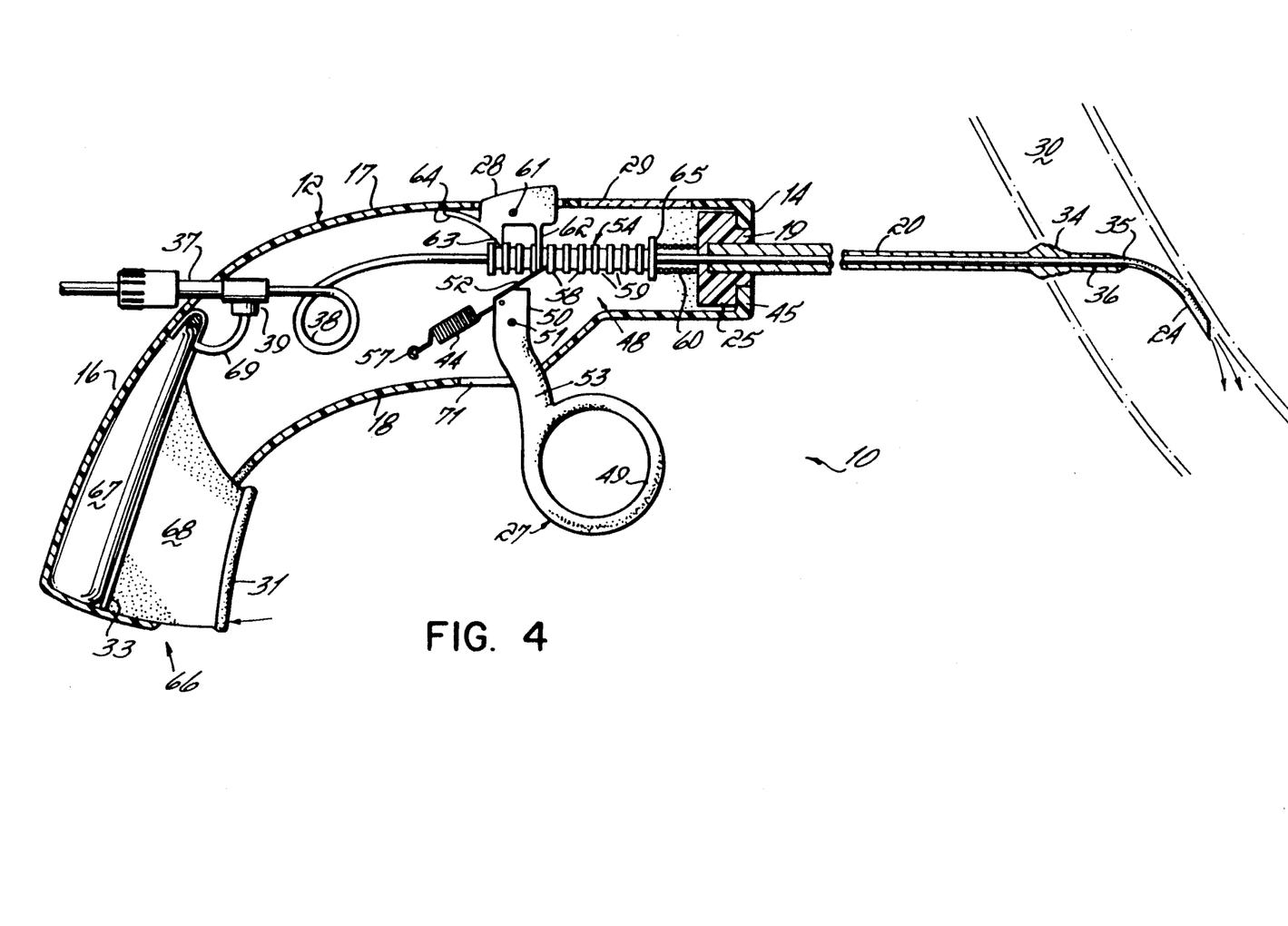
FIG. 4 is a cross-sectional view of the preferred embodiment of the invention just prior to the injection of the contrast media into the cystic duct during the cholangiogram procedure.

To inject contrast media into the cystic duct, the surgeon pushes actuator 31 rearwardly towards housing 12 to rotate plunger 33 against collapsible reservoir 67 to expel contrast media from the reservoir through conduit 69 to valve 39 as shown in FIG. 4. Valve 39 is preferably a pressure actuated valve that closes the flow from leur lock 37 in response to the flow of contrast media from reservoir 67. The contrast media flows through catheter 24 into the cystic duct 30. The construction of valve 39 is well known within the art.

The length of plunger arm 68 is sized so an actuator stroke of approximately one-half of its length produces a volume of contrast media sufficient for one cholangiogram. In the preferred embodiment of the invention, the plunger arm is approximately 4 inches long so a two inch stroke generates a media injection of approximately 10-15 cc. The surgeon holds the actuator at the half way point while the technician changes film for the second cholangiogram and then pushes the actuator until it contacts lower surface 18 to provide the media injection for the second x-ray.

After the cholangiograms are taken, the catheter may be removed from the cystic duct by pushing release arm 28. As shown in FIG. 4, collar 54 is advanced to a position where catheter 24 is extended from cannula 20 by approximately 4 centimeters. The surgeon may now depress lock and release arm 28 with sufficient pressure to clockwise rotate the arm about pivot point 61 which compresses locking arm 63 against housing 12. The surgeon can easily exert enough pressure against resilient locking arm 63 so the locking arm clears ridges 58. As this happens, the inwardly extending end of release member 62 pushes against the top edge of driving link 52 to drive link 52 vertically downward and disengage it from collar 54. Because the laterally offset portion of member 62 lies outside the diameter of ridge 58, the collar is urged rearwardly by spring 60 to retract catheter 24 into cannula 20. The rearward movement of collar 54 caused by spring 60 is halted when the laterally offset position of member 62 contacts forwardmost ridge 58. When link arm 28 is released, locking member 63 rotates counterclockwise to re-engage collar 54. Cannula 20 may then be removed from the abdominal cavity and trocar.

The instrument shown in FIG. 1 provides a surgical instrument that fits easily in the grasp of a human hand. All aspects of the procedure necessary to perform a cholangiogram—cutting the cystic duct, inserting the cannula and catheter into the duct, pumping contrast media into the duct and removing the cannula from the duct—can be performed singlehandedly by a surgeon with this instrument. The controls for the various functions of the instrument are conveniently located for independent control by different fingers of the surgeon's hand. For example, trigger 27 is squeezed typically by the index digit of the hand to advance the catheter through the cannula. Actuator 31 can be pushed rearwardly towards housing 12 to expel contrast media from reservoir 67 into the catheter by the last three fingers. When the cholangiogram has been taken, the thumb may be used to push lock and release arm 28 so spring 60 withdraws the catheter into cannula 20. The incorporation of all of the functions necessary to perform a cholangiogram into a single instrument and conveniently locating all the controls for the functions so they may be operated independently by the fingers of the surgeon's hand is an important advantage of the present invention.

Each full squeeze of trigger 27 advances a predetermined length of catheter 24 from cannula 20 when catheter 24 is initially aligned with the sharpened opening of the lumen at angled end 35. The tactile feedback provided from the trigger squeeze permits the surgeon to count each squeeze to know the depth of catheter insertion without removing his eyes from the CRT. Additionally, the locking mechanism produces an audible click as collar 54 is halted and as trigger 27 returns to its forward position. This click provides auditory confirmation of the trigger squeeze count. Should the surgeon inadvertently lose count of the clicks and trigger pulls, the visual window can be checked to see how far the catheter is extended.

While the present invention has been illustrated by the description of a preferred embodiment and while the embodiment has been described in considerable detail, it is not the intention of the applicant to be restricted or any way limit the scope of the appended claims to such detail. Additional advantages and modifications will be readily apparent to those skilled in the art. The invention in its broader aspects is therefore not limited to the specific details, representative apparatus and method, and illustrative examples shown and described. Accordingly departure may be made from such details without departing from the spirit or scope of applicant's general inventive concept.

What is claimed is:

1. A device for performing a cholangiogram during a laparoscopic surgical procedure comprising:
   a cannula having a lumen extending between first and second ends, said first end of said cannula having a sharpened edge at he juncture of said cannula and said lumen;
   a threaded bulge proximate said first end of said cannula; and
   a hollow catheter having first and second ends and being concentrically located and slidable within said lumen of said cannula, said first end of said catheter being within said cannula and said second end extending from said second end of said cannula whereby said sharpened edge of said cannula may be used to cut an incision into a cystic duct and said threaded bulge facilitates the insertion of the cannula into the cystic duct to form a seal so the catheter may be slid towards said first end and through the incision into the cystic duct.

2. The device of claim 1 further comprising:
   means for advancing said catheter within said cannula to extend said first end of said catheter beyond said first end of said cannula.

3. The device of claim 2 further comprising:
   means for locking said catheter in fixed relation to said cannula.

4. The device of claim 2 further comprising:
   means for determining the distance said first end of said catheter is extended beyond said first end of said cannula whereby a surgeon advancing said catheter by said advancing means knows when said catheter is extended a predetermined distance from said first end of said cannula.

5. The device of claim 2 further comprising:
   means for selectively connecting said catheter to one of two fluid sources whereby said catheter may be used to inject either one of the two fluids contained within the fluid sources.

6. The device of claim 1 further comprising:
   a dial having a hub connected to a wheel, said second end of said cannula being mounted within said hub whereby rotating said wheel of said dial rotates said hub and said cannula to advance said threaded bulge into the incision.

7. A method for performing cholangiogram during a laparoscopic surgical procedure comprising the steps of:
   opening a cystic duct with a sharpened edge at a juncture of a lumen within a cannula at one end of the cannula;
   advancing a hollow catheter, concentrically located within the cannula, through the opening in the cystic duct into the cystic duct;
   inserting the end of the cannula and a threaded bulge of the cannula proximate the inserted end into the cystic duct to substantially stop the flow of fluids through the opening of the cystic duct about the cannula;

rotating the cannula to advance the threaded bulge on the cannula proximate the inserted end to facilitate the insertion of the cannula and threaded bulge;

injecting contrast media into the cystic duct through the hollow catheter;

radiographically taking a cholangiogram; and retracting the catheter and cannula from the cystic duct.

8. A hand held apparatus for performing a cholangiogram during a laparoscopic surgical procedure comprising:

a housing shaped and sized to fit a human hand, said housing having a forward and a rearward portion;

a cannula having a lumen extending between first and second ends, said first end being mounted to said forward portion of said housing and said second end extending away from said housing, said second end of said cannula having a sharpened edge at the juncture of said lumen and said second end of said cannula, said second end having a bulge proximate said sharpened edge;

a hollow catheter having first and second ends, said catheter being concentrically located within said cannula with said first end of said catheter proximate said second end of said cannula and said second end of said catheter extending through said housing and extending from said rearward portion of said housing.

9. The device of claim 8 wherein said bulge is threaded whereby turning said cannula screws said second end and said bulge of said cannula into the incision.

10. The device of claim 8 further comprising:

a dial rotatably mounted within said housing, said dial having a wheel connected to a hub, said first end of said cannula being mounted within said hub whereby turning said wheel of said dial rotates said cannula to screw said second end and said bulge into the incision to prevent fluids from leaking from the incision.

11. The device of claim 8 further comprising:

means for advancing said catheter within said cannula to extend said first end of said catheter from said second end of said cannula.

12. The device of claim 11 further comprising:

means for viewing a portion of said catheter advancing means, said viewing means being mounted in said housing near said forward portion, said viewing means being lineated whereby the juxtaposition of said portion of said catheter advancing means viewed through said viewing means with said lineation of said viewing means may be used to determine how far said catheter has been extended from said second end of said cannula.

13. The device of claim 8 further comprising:

means for selecting fluid from one of two fluid sources for injection through said catheter, said selecting means being operatively connected to said second end of said catheter;

a reservoir for holding one of the two fluid sources, said reservoir being operatively connected to said selecting means; and means for expelling the fluid in said reservoir through said selecting means and said catheter, said expelling means being mounted to said housing and operatively connected to said reservoir.

14. The device of claim 13 wherein said reservoir is collapsible and said expelling means further comprises:

plunger means hingedly mounted to said housing and lying adjacent at least one side of said reservoir; and actuating means connected to said plunger means and extending from said housing whereby said actuating means may be pressed to urge said plunger means against said collapsible reservoir to expel the fluid from said reservoir.

15. The device of claim 11 wherein said expelling means and said advancing means are located on said housing so that said expelling means and said advancing means may be independently operated by different digits of one hand.

* * * * *